(12) United States Patent
Yang et al.

(10) Patent No.: US 9,422,254 B2
(45) Date of Patent: Aug. 23, 2016

(54) METHOXYACRYLATE-BASED FUNGICIDE AND METHODS FOR PREPARING AND USING THE SAME

(75) Inventors: Guangfu Yang, Wuhan (CN); Peiliang Zhao, Wuhan (CN); Wei Huang, Wuhan (CN); Zuming Liu, Wuhan (CN); Hualong Wu, Jiaxing (CN)

(73) Assignee: Central China Normal University, Wuhan (CN)

( * ) Notice: Subject to any disclaimer, the term of this patent is extended or adjusted under 35 U.S.C. 154(b) by 313 days.

(21) Appl. No.: 12/843,899

(22) Filed: Jul. 27, 2010

(65) Prior Publication Data

US 2010/0292285 A1 Nov. 18, 2010

Related U.S. Application Data

(63) Continuation of application No. PCT/CN2009/071301, filed on Apr. 16, 2009.

(30) Foreign Application Priority Data

May 8, 2008 (CN) .......................... 2008 1 0047642

(51) Int. Cl.
| | |
|---|---|
| *A01N 43/74* | (2006.01) |
| *C07D 277/74* | (2006.01) |
| *A01P 3/00* | (2006.01) |
| *A01N 43/78* | (2006.01) |

(52) U.S. Cl.
CPC ............ *C07D 277/74* (2013.01); *A01N 43/74* (2013.01); *A01N 43/78* (2013.01)

(58) Field of Classification Search
None
See application file for complete search history.

(56) References Cited

U.S. PATENT DOCUMENTS

| | | | | |
|---|---|---|---|---|
| 3,857,959 A | * | 12/1974 | Rosenwald | 514/731 |
| 4,356,179 A | * | 10/1982 | Petteruti | 514/245 |
| 5,304,530 A | * | 4/1994 | Cliff et al. | 504/266 |
| 5,677,303 A | * | 10/1997 | Curtze et al. | 514/237.5 |
| 6,617,330 B2 | * | 9/2003 | Walter | 514/258.1 |
| 2003/0055096 A1 | * | 3/2003 | Oguri | 514/394 |
| 2005/0220834 A1 | * | 10/2005 | Wang et al. | 424/405 |

FOREIGN PATENT DOCUMENTS

CN 101248794 A * 8/2008 ............. A01N 47/18

OTHER PUBLICATIONS

"Glycidyl Ether Reactions with Amines" by Shechter et al., Indus. Eng. Chem. 48, 94-97 (1956).*
"Bioisosterism: A Rational Approach to Drug Design" by Patani et al., Chem. Rev. 96, 3147-76 (1996).*
"Bioisosterism" in "The Organic Chemistry of Drug Design and Drug Action" by Silverman, Academic Press (New York), pp. 19-23 (1992).*

* cited by examiner

*Primary Examiner* — Theodore R West
(74) *Attorney, Agent, or Firm* — Matthias Scholl, PC; Matthias Scholl

(57) ABSTRACT

A pharmaceutical composition of fungicide including at least a compound represented by Formula (I).

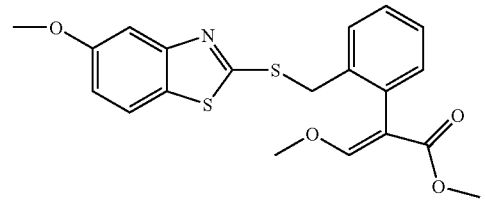

The pharmaceutical composition of fungicide can further include an emulsifier, a cosolvent, a stabilizer, and a solvent. The fungicide can prevent and treat powdery mildew, downy mildew, gray mold, brown spot, scab of vegetables and fruits, southern leaf blight of corn, rice false smut, citrus stem-end rot, and rape sclerotinia rot, with high efficiency, low toxicity, and relative environmental friendliness. A method of preparing the fungicide and a method of using thereof are also provided.

3 Claims, 1 Drawing Sheet

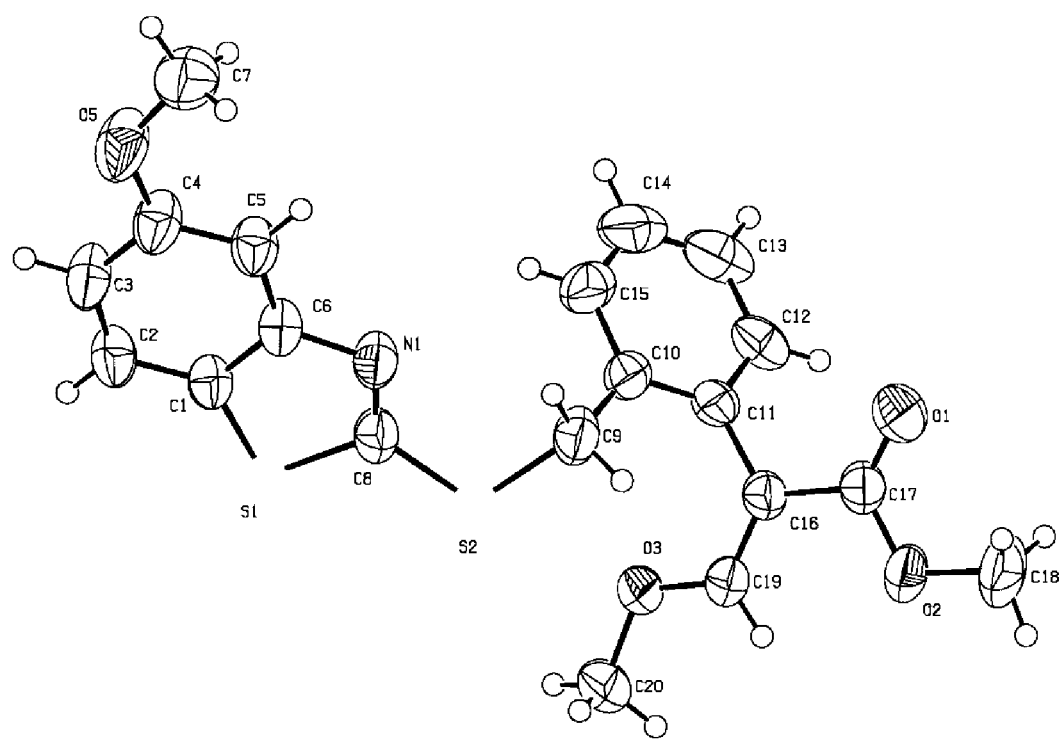

METHOXYACRYLATE-BASED FUNGICIDE AND METHODS FOR PREPARING AND USING THE SAME

CROSS-REFERENCE TO RELATED APPLICATIONS

This application is a continuation of International Patent Application No. PCT/CN2009/071301 with an international filing date of Apr. 16, 2009, designating the United States, and further claims priority benefits to Chinese Patent Application No. 200810047642.1 filed May 8, 2008. The contents of all of the aforementioned applications, including any intervening amendments thereto, are incorporated herein by reference.

BACKGROUND OF THE INVENTION

1. Field of the Invention

The invention relates to a methoxyacrylate, the preparation, fungicides containing same, and the use as a fungicide

2. Description of the Related Art

The methoxyacrylate fungicides were firstly developed by Zeneca Co., Ltd. (Syngenta) in 1980s and exhibit advantages such as high efficiency, broad-spectrum, and relative environmental friendliness. The structure unit of β-methoxyacrylate is the pharmacophore of this kind of fungicide. However, with the increase of fungus having drug resistance, a more powerful fungicide is desired.

SUMMARY OF THE INVENTION

In view of the above-described problems, it is one objective of the invention to provide a pharmaceutical composition of fungicide.

It is another objective of the invention to provide a method for preparing a pharmaceutical composition of fungicide.

It is still another objective of the invention to provide a method for preventing and treating a plant disease.

To achieve the above objectives, in accordance with one embodiment of the invention, there is provided a pharmaceutical composition of fungicide comprising a compound represented by Formula (I): (E)-methyl 3-methoxy-2-(2-((5-methoxy-benzothiazol-2-ylthio)methyl)phenyl)acrylate.

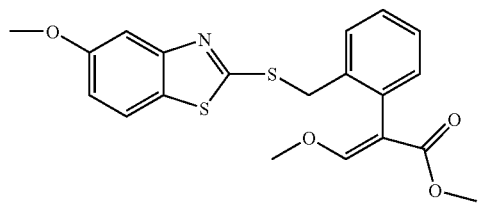

I

In a class of this embodiment, the compound is mixed with an emulsifier, a cosolvent, a stabilizer, and a solvent to yield an emulsifiable concentrate. The emulsifiable concentrate can be used to prevent and treat powdery mildew, downy mildew, gray mold, brown spot, scab of vegetables and fruits, southern leaf blight of corn, rice false smut, citrus stem-end rot, and rape sclerotinia rot. The emulsifiable concentrate has effect even on resistant strains, with high efficiency, low toxicity, and environmentally friendliness.

In a class of this embodiment, the pharmaceutical composition of fungicide comprises between 5 and 10 wt % of the compound represented by Formula (I), between 0 and 15 wt % of the emulsifier, between 0 and 30 wt % of the cosolvent, between 0 and 2 wt % of the stabilizer, and between 0 and 65.5 wt % of the solvent.

In a class of this embodiment, the pharmaceutical composition of fungicide comprises between 5 and 10% wt of the compound represented by Formula (I), 10% wt of the emulsifier, between 20 and 30 wt % of the cosolvent, 2% wt of the stabilizer, and between 48 and 65.5% wt of the solvent.

In a class of this embodiment, the emulsifier is pesticide emulsifier No. 500, pesticide emulsifier No. 33, pesticide emulsifier No. 700, pesticide emulsifier No. 601, sodium $C_{8-20}$alkyl sulfate, Tween 80, Tween 60, ammonium styryl polyethenoxy ether sulfate, pesticide emulsifier No. 300, pesticide emulsifier No. 600 having a polymerization degree of 15-30, styrenephenol polyethenoxy polyoxypropylene ether, nonylphenol polyethenoxy ether, alkylphenol formal polyethenoxy ether, diphenol polyethenoxy ether, or a mixture thereof.

In a class of this embodiment, the solvent is toluene, xylene, methanol, ethanol, isopropanol, or a mixture thereof.

In a class of this embodiment, the cosolvent is dichloromethane, N, N-dimethylformamide (DMF), dimethylacetamide (DMAC), dimethyl sulfoxide (DMSO), acetone, pyrrolidone, or a mixture thereof.

In a class of this embodiment, the stabilizer is epoxidized soybean oil, epoxy chloropropane, 3-chloro-1,2-propylene oxide, butyl glycidyl ether, phenyl glycidyl ether, cresyl glycidyl ether, polyethylene glycol diglycidyl ether, sodium sorbitol, 0.1 wt. % citric acid aqueous solution, 0.1 wt. % benzoic acid aqueous solution, or 0.1 wt. % sodium dihydrogen phosphate buffer.

In accordance with another embodiment of the invention, there provided is a method for preparing a pharmaceutical composition of fungicide comprising mixing the compound of Formula (I), an emulsifier, a cosolvent, a stabilizer, and a solvent and stiffing uniformly.

In a class of this embodiment, upon mixing and stirring, the compound of Formula (I) is between 5 and 10 weight parts, the emulsifier is between 0 and 15 weight parts, the cosolvent is between 0 and 30 weight parts, the stabilizer is between 0 and 2 weight parts, and the solvent is between 0 and 65.5 weight parts. The resultant emulsifiable concentrate comprises between 5 and 10 wt. % of the compound of Formula (I), between 0 and 15 wt. % of the emulsifier, between 0 and 30 wt. % of the cosolvent, between 0 and 2 wt. % of the stabilizer, and between 0 and 65.5 wt. % of the solvent.

In a class of this embodiment, upon mixing and stiffing, the compound of Formula (I) is between 5 and 10 weight parts, the emulsifier is 10 weight parts, the cosolvent is between 20 and 30 weight parts, the stabilizer is 2 weight parts, and the solvent is between 48 and 65.5 weight parts. The resultant emulsifiable concentrate comprises between 5 and 10 wt. % of the compound of Formula (I), 10 wt. % of the emulsifier, between 20 and 30 wt. % of the cosolvent, 2 wt. % of the stabilizer, and between 48 and 65.5 wt. % of the solvent.

The emulsifier, cosolvent, stabilizer, and solvent are the same as defined above.

In a class of this embodiment, the compound of Formula (I) is prepared as follows.

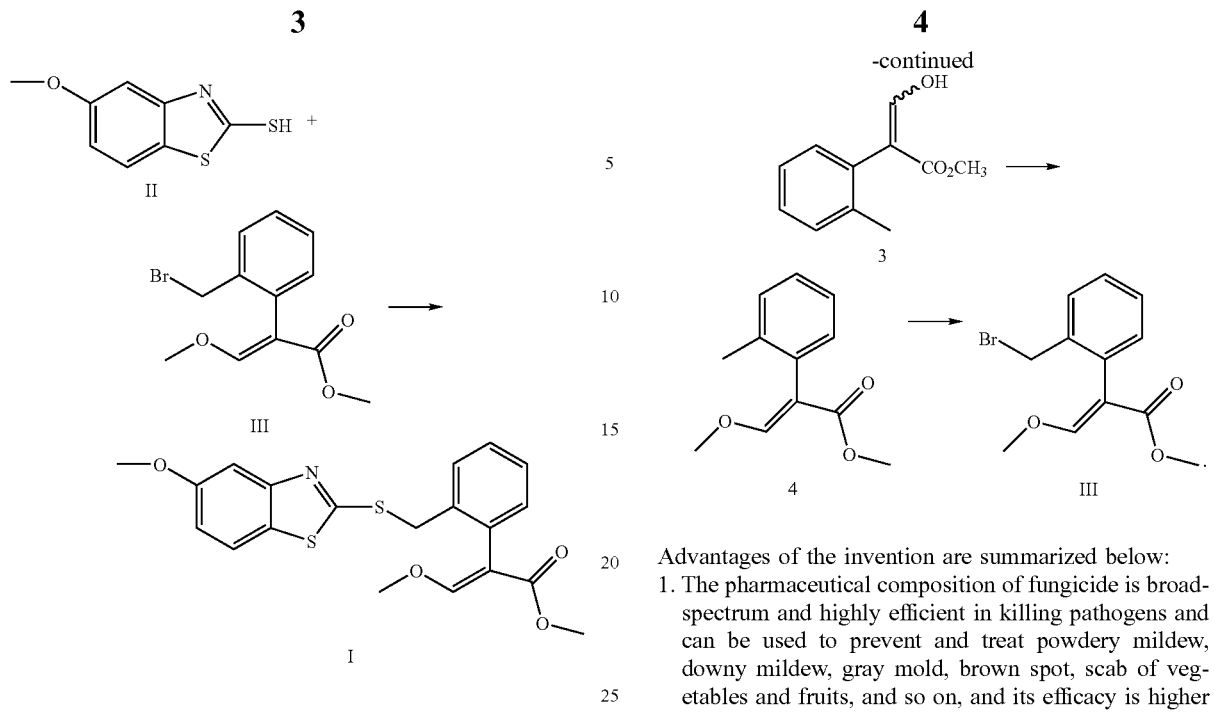

The intermediate (II) reacts with the intermediate (III) in the presence of a base. The base is sodium hydroxide, potassium hydroxide, sodium carbonate, or potassium carbonate. A reaction solvent is water, methanol, ethanol, N,N-dimethyl formamide, or a mixture thereof, particularly a mixed solvent of water and N, N-dimethyl formamide with a volume ratio of 5:1. A reaction temperature is from room temperature to the boiling point of the solvent. A reaction time is between 4 and 6 hrs. A molar ratio of the intermediate (II) to the intermediate (III) to sodium hydroxide is 1:1:1.2.

In a class of this embodiment, the intermediate (II) is prepared as follows.

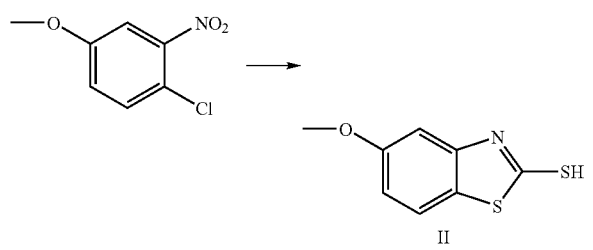

1-chloro-4-methoxy-2-nitrobenzene, carbon disulfide, and sodium polysulfide are mixed and refluxed for between 4 and 6 hrs to yield the intermediate (II).

In a class of this embodiment, the intermediate (III) is prepared following the method disclosed in Pestic. Sci., 1991, 31, 499-519, the steps are:

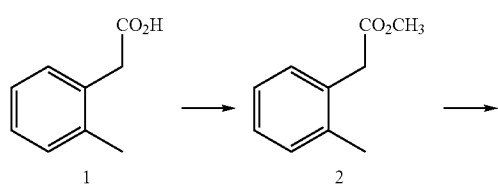

Advantages of the invention are summarized below:
1. The pharmaceutical composition of fungicide is broad-spectrum and highly efficient in killing pathogens and can be used to prevent and treat powdery mildew, downy mildew, gray mold, brown spot, scab of vegetables and fruits, and so on, and its efficacy is higher than that of azoxystrobin and kresoxim-methyl;
2. The pharmaceutical composition of fungicide is particularly effective on powdery mildew of melons; results of field trial show that 3.75 g/acre of active ingredients can effectively control powdery mildew of melons; and
3. The pharmaceutical composition of fungicide has effect even on resistant strains and no cross resistance occurs.

BRIEF DESCRIPTION OF THE DRAWINGS

The invention is described hereinbelow with reference to accompanying drawings, in which the sole FIGURE is a schematic diagram of crystal structure of the compound of Formula (I) according to one embodiment of the invention.

DETAILED DESCRIPTION OF THE EMBODIMENTS

For further illustrating the invention, experiments detailing a pharmaceutical composition of fungicide, a preparation method and use thereof are described below. It should be noted that the following examples are intended to describe and not to limit the invention.

Example 1

Preparation of Compound of Formula (I)

(E)-methyl 3-methoxy-2-(2-((5-methoxy-benzothiazol-2-ylthio)methyl)phenyl)acrylate Preparation of Intermediate (II)

244 g of sodium polysulfide solution was mixed with 30 g of 1-chloro-4-methoxy-2-nitrobenzene, and then 20 mL of carbon disulfide was added with stirring. The mixture was heated and refluxed for about 5 hrs and a yellow solid precipitated. The mixture was filtered and the filtrate was diluted with water to 1000 mL. An orange yellow solution was obtained. The solution was neutralized with hydrochloric acid (6M) to yield a light yellow solid. The solid was filtered, washed with water, and dried. 29.4 g of products was obtained with a yield of 93.1%.

Preparation of Intermediate (2): methyl 2-o-tolylacetate

To a flask (1000 mL), 120 g of 2-methylphenylacetic acid and 400 mL of anhydrous methanol were added, and then 24 mL of concentrated sulfuric acid was further added with stiffing. The mixture was heated with an oil bath and refluxed. The reaction was monitored with thin layer chromatography (TLC) until the reactants were basically consumed. Subsequently, the solvent was removed by vacuum distillation. The residue was dumped into 400 mL of water and extracted with 400 mL of ethyl acetate. The organic layer was washed with water (2×200 mL), dried over anhydrous magnesium sulfate, and concentrated under reduced pressure. A light yellow oily product was obtained. The light yellow oily product was further distilled under vacuum condition to yield 117.3 g of a colorless oily product (135-140° C., 16 mmHg) with a yield of 92%.

Preparation of Intermediate (3): methyl 3-hydroxy-2-o-tolylacrylate

To a three neck flask (1000 mL), 50 g of methyl 2-o-tolylacetate and 600 mg of toluene were added, and then 54.3 g of sodium methoxide was further added with stiffing. The mixture was cooled with an ice-water bath to less than 10° C., and then a mixture of methyl formate (65 mL) and toluene (50 mL) was dripped. After that, the ice-water bath was removed and the temperature was raised slowly to room temperature. The solution was allowed to react with stirring for 12 hrs, and then dumped into 1000 mL of water, shaken, standed for demix. The organic layer was extracted with 500 mL of water twice. The water layer was combined, acidized with 6M hydrochloric acid to pH value of 4-5, extracted with ethyl acetate, dried with anhydrous magnesium sulfate, and distilled under vacuum condition to yield 55.9 g of light red oily product with a yield of 95%.

Preparation of Intermediate (4): methyl 3-methoxy-2-o-tolylacrylate

To a flask (1000 mL), 48 g of methyl 3-hydroxy-2-o-tolylacrylate, 54.4 g of potassium carbonate, and 500 mL of ethylene glycol dimethyl ether were added. The mixture was stirred at room temperature for an hour, and then 36 mL of dimethyl sulfate was added. The mixture was allowed to react for between 6 and 8 hrs with stiffing at room temperature. The reaction was monitored with thin layer chromatography (TLC) until the reactants were basically consumed. Subsequently, the mixture was filtered, the solvent was removed by vacuum distillation, the residue was washed with water (1000 mL), extracted with ethyl acetate (2×300 mL), dried with anhydrous sodium sulfate and concentrated under reduced pressure to yield a light yellow oily product with a yield of 97%.

Preparation of Intermediate (III)

39.14 g of methyl 3-methoxy-2-o-tolylacrylate, 41.3 g of N-bromosuccinimide (NBS), and 1.44 g of azobisisobutyronitrile (AIBN) were mixed with 200 mL of carbon tetrachloride. The mixture was lighted with an incandescent lamp for 6 hrs, cooled, and filtered. The filtrated was concentrated under reduced pressure to yield a yellow viscous material which could be used directly for further reaction.

Preparation of the Compound of Formula (I)

To 350 mL of an aqueous solution having 8.0 g of sodium hydroxide, 31.8 g of Intermediate (II) was added and stirred for 20 min. Subsequently, 70 mL of N, N-dimethylformamide (DMF) solution having 54 g of Intermediate (III) was added. The mixture was stirred at room temperature for 6 hrs and water added until the total volume was 1000 mL. The solution was extracted with dichloromethane, dried over anhydrous sodium sulfate, and the product purified by chromatography over silica gel eluted with ethyl acetate/hexane, 52.1 g of a yellow solid was obtained with a total yield was 80.5%. m.p. 85-87° C. $^1$H NMR (400 MHz, CDCl$_3$) δ: 3.72 (s, 3H, COOCH$_3$), 3.82 (s, 3H, =CH—OCH$_3$), 3.84 (s, 3H, OCH$_3$), 4.52 (s, 1H, CH$_2$), 6.94 (dd, J=2.4 Hz, J=8.8 Hz, 1H, ArH), 7.16 (t, J=4.6 Hz, 1H, ArH), 7.29-7.31 (m, 2H, ArH), 7.40 (d, J=2.8 Hz, 1H, ArH), 7.54-7.61 (m, 3H, =CH—OCH$_3$, ArH). EI MS: m/z (%) 401 (M+, 4), 369(19), 205 (11), 167 (24), 144 (100), 101 (37). Anal. Calcd for C$_{20}$H$_{19}$NO$_4$S$_2$: C, 59.83; H, 4.77; N, 3.49. Found: C, 59.89; H, 5.01; N, 3.27.

FIG. 1 shows the crystal structure of the compound of Formula (I).

Example 2

Evaluation on Indoor Bioactivity of Compound of Formula (I)

To verify the bioactivity of the compound of Formula (I), experiments evaluating indoor bioactivity comprising fungicidal activity test on potted plants at room temperature, fungicidal spectrum assay (in vitro), and in vivo microscreening assay are carried out.

1. Fungicidal Activity Assay on Potted Plants at Room Temperature

Take cucumber downy mildew and powdery mildew as examples, the assay were carried out as follows:

1) *Pseudoperonospora cubensis*: Pathogen of Cucumber Downy Mildew

Two cucumber seedlings (the growing point had been removed) having the same growth status and in the true leaf stage were collected, sprayed with the compound of Formula (I), and dried naturally for 24 hrs for inoculation. Fresh cucumber leaves infected by downy mildew were collected, and sporangium on the back was rinsed with distilled water (about 10° C.) dipped with a brush. The obtained sporangium was prepared into a suspension (2-3×10$^5$ cells/mL). The suspension was sprayed uniformly with an inoculation sprayer (0.1 MPa) to the naturally-dried cucumber seedlings. Subsequently, the seedlings were cultured in an artificial climate chamber. The relative humidity was maintained at 100%, with temperature of between 15 and 20° C. 24 hrs later, the relative humidity was maintained at 90%, with temperature of between 15 and 24° C. 5 days later, compared with the control, the disease of the cucumber seedlings was graded. Based on the resultant disease index, the efficacy was calculated.

2) *Sphaerotheca uliginea*: Pathogen of Cucumber Powdery Mildew

A cucumber seedling having uniform growth status and in the true leaf stage was collected, sprayed with the compound of Formula (I), and dried in the shade for 24 hrs. Fresh spore was collected from cucumber leaves infected by *Sphaeroth-*

*eca uliginea*, filtered with a double-layer gauze, and prepared into a suspension ($1.0 \times 10^5$ cells/mL). The suspension was sprayed to the dried cucumber seedling. Subsequently, the inoculated seedling was dried naturally and cultured under light in a thermostatic chamber (21-23° C.). 7-8 days later, compared with the blank control, the disease of the cucumber seedlings was graded. Based on the resultant disease index, the efficacy was calculated.

3) Calculation Method

The grading standard follows "Guidelines on efficacy evaluation of pesticides", and the efficacy is calculated on the basis of the disease index.

Disease index=Σ(total amount of diseased leaves of a grade×value of the grade)×100/(total amount of leaves×9);

Efficacy (%)=(disease index of blank control−disease index of experiment group)×100/disease index of blank control The results are listed in Table 1 and Table 2.

TABLE 1

Efficacy of the compound of Formula (I) on potted cucumber infected by downy mildew and powdery mildew

| Concentration | Efficacy (%) | |
|---|---|---|
| (mg/L) | Cucumber downy mildew | Cucumber powdery mildew |
| 200 | 100 | 100 |
| 100 | 100 | 100 |
| 50 | 100 | 100 |
| 25 | 94.16 | 100 |
| 12.5 | 87.34 | 97.22 |

TABLE 2

Results of secondary screening of the compound of Formula (I) on potted cucumber infected by downy mildew and powdery mildew

| Concentration | Cucumber downy mildew | | Cucumber powdery mildew | |
|---|---|---|---|---|
| (mg/L) | Efficacy (%) | $EC_{50}/EC_{90}$ | Efficacy (%) | $EC_{50}/EC_{90}$ |
| 50 | 100 | 1.52/9.76 | 100 | 0.96/3.87 |
| 25 | 98.15 | | 100 | |
| 12.5 | 91.50 | | 98.50 | |
| 6.25 | 82.89 | | 97.22 | |
| 3.125 | 69.92 | | 85.24 | |

2. Fungicidal Spectrum Assay (In Vitro)

To broaden the fungicidal spectrum of the compound of Formula (I), as targets the following 20 pathogens were assayed in vitro. The results showed the compound of Formula (I) had a wide fungicidal spectrum, particularly effective on *Helminthosporum maydis*, *Ustilaginoidea virens*, and *Diaporthe medusa* in vitro. The 20 pathogens and resultant plant diseases were:

Rice sheath blight (*Rhizoctonia solani*),
Cucumber gray mold (*Botrytis cinerea*),
Rape sclerotinia rot (*Sclerotinia sclerotirum*),
Wheat scab (*Gibberella zea*),
Rice blast (*Pyricularia oryzae*),
Cucumber anthracnose (*Colletotrichum lagenarium*),
Potato late blight (*Phytophthora infestans*),
Pepper *phytophthora* blight (*Phytophthora capsici*),
Southern leaf blight of corn (*Helminthosporum maydis*),
Tomato early blight (*Alternaria solani*),
Apple ring rot (*Botryosphaeria berengeriana*),
Tobacco brown spot (*Alternaria alternata*),
Banana leaf spot (*Helminthosporium torulosum*),
Wheat sheath blight (*Rhizoctonia solani*),
Wheat root rot (*Bipolaris sorokiniana*),
Cotton wilt (*Fusarium oxysporum*),
Citrus stem-end rot (*Diaporthe medusae*),
Cotton boll rot (*Fusarium moniliforme*),
Rice false smut (*Ustilaginoidea virens*), and
Peanut brown spot (*Cercospora arachidicola*).

Measurement of In Vitro Inhibitory Rate 5 wt % formulation of the active compound of Formula (I) was prepared into a solution (300 mg/L). To a sterilized Erlenmeyer flask, 2 mL of the solution and 18 mL of PDA culture medium (50° C.) were added. The mixture was shaken uniformly and dumped into two dishes whose diameter was 9 cm to yield two toxic PDA culture mediums having a concentration of 30 mg/L. Various cultured pathogens were punched at the edge of colony by a puncher having a diameter of 5 mm respectively, and the obtained pieces were transferred to the center of the toxic PDA culture medium by an inoculating needle and cultured in an incubator at 25° C. Repeat the above steps. According to the growth status of CK colony, the colony diameter of pathogens was measured by crossing method with a caliper and thereby a corrected inhibition percentage was calculated.

Calculation of Efficacy

For each colony, diameter was measured twice by crossing method and the average was practicable. The colony growth inhibition rate was calculated as follows:

Colony growth inhibition rate %=(diameter of CK colony−diameter of target colony)×100/diameter of CK colony The results are listed in Table 3.

TABLE 3

Fungicidal activity (in vitro) of compound of formula (I) on 20 pathogens

| | Inhibition rate (%) | | |
|---|---|---|---|
| Pathogen | Concentration (mg/L) 30 | Concentration (mg/L) 3 | Concentration (mg/L) 0.3 |
| *Rhizoctonia solani* | 68.93 | 62.14 | 42.72 |
| *Botrytis cinerea* | 54.85 | 42.73 | 42.31 |
| *Sclerotinia sclerotirum* | 80.00 | 61.03 | 50.77 |
| *Gibberella zea* | 54.59 | 45.87 | 34.86 |
| *Pyricularia oryzae* | 82.61 | 56.52 | 23.60 |
| *Colletotrichum lagenarium* | 50.72 | 44.20 | 42.03 |
| *Phytophthora infestans* | 38.00 | 33.74 | 15.34 |
| *Phytophthora capsici* | 28.85 | 23.07 | 0 |
| *Helminthosporum maydis* | 100 | 100 | 86.11 |
| *Alternaria solani* | 43.92 | 39.19 | 32.43 |
| *Botryosphaeria berengeriana* | 63.64 | 49.65 | 44.06 |
| *Alternaria alternata* | 43.14 | 41.83 | 37.25 |
| *Helminthosporium torulosum* | 21.43 | 18.45 | 11.31 |
| *Rhizoctonia solani* | 68.52 | 44.44 | 22.22 |
| *Bipolaris sorokiniana* | 43.75 | 40.63 | 18.75 |
| *Fusarium oxysporum* | 43.70 | 36.13 | 29.41 |
| *Fusarium moniliforme* | 43.58 | 30.77 | 9.60 |
| *Diaporthe medusae* | 87.23 | 80.14 | 55.32 |
| *Ustilaginoidea virens* | 100 | 100 | 74.77 |
| *Cercospora arachidicola* | 40.48 | 35.71 | 30.95 |

Following the above method, as targets 17 pathogens originated from tropical plants were tested. The pathogens were *Rhizopus* sp., *Aspergillus, Colletotrichum gloeosporioides* Penz, Banana *Fusarium wilt, Colletouichum coccodes*, Hughas, *B. heveas*, Cucumber mosaic virusstrain banana, Banana Sigatoka Leaf Spot Disease, *Colletotrichum gloeosporioides, Colletotrichum musae* (Berk & Curt) Arx, *Botryodiplodia theobromae, Cladosporium cucumerinum* Ellis et Arthur, *Periconia hevenae, Colletotrichum gloeosporioides, B. cinerea, Diplodia natalensis*, and *Curvularia*. The results are listed in Table 4.

TABLE 4

Fungicidal activity (in vitro) of compound of formula (I) on 17 pathogens originated from tropical plants

| Pathogen | Concentration (mg/L) | Inhibition rate (%) | $EC_{50}$ |
|---|---|---|---|
| *Rhizopus* sp. | 20 | 88.5 | 4.1774 |
|  | 15 | 83.6 |  |
|  | 10 | 69.3 |  |
|  | 5 | 53.1 |  |
|  | 1 | 18.4 |  |
| *Aspergillus* | 50 | 86.12 | 5.0287 |
|  | 25 | 71.43 |  |
|  | 10 | 58.37 |  |
|  | 5 | 47.76 |  |
|  | 1 | 27.35 |  |
|  | 0.1 | 10.61 |  |
| *Colletotrichum gloeosporioides* Penz | 50 | 80.93 | 4.6266 |
|  | 25 | 69.26 |  |
|  | 10 | 54.86 |  |
|  | 5 | 50.19 |  |
|  | 1 | 31.13 |  |
|  | 0.1 | 16.73 |  |
| Banana *Fusarium* wilt | 50 | 80.43 | 9.2172 |
|  | 25 | 67.62 |  |
|  | 10 | 60.50 |  |
|  | 5 | 30.25 |  |
|  | 1 | 13.52 |  |
| *Colletouichum coccodes*. Hughas | 25 | 83.54 | 7.1258 |
|  | 15 | 61.28 |  |
|  | 5 | 42.07 |  |
|  | 2 | 22.26 |  |
|  | 0.1 | 10.06 |  |
| *B. heveas* | 15 | 81.44 | 1.9902 |
|  | 10 | 70.45 |  |
|  | 5 | 61.36 |  |
|  | 1 | 43.94 |  |
|  | 0.1 | 9.09 |  |
| Cucumber mosaic virusstrain banana | 15 | 84.84 | 1.9212 |
|  | 10 | 76.64 |  |
|  | 5 | 62.30 |  |
|  | 1 | 40.16 |  |
|  | 0.1 | 9.84 |  |
| Banana Sigatoka Leaf Spot Disease | 20 | 85.77 | 1.4987 |
|  | 10 | 77.90 |  |
|  | 5 | 63.67 |  |
|  | 1 | 43.45 |  |
|  | 0.1 | 17.23 |  |
| *Colletotrichum gloeosporioides* | 20 | 83.16 | 1.9699 |
|  | 10 | 69.36 |  |
|  | 5 | 55.89 |  |
|  | 1 | 42.42 |  |
|  | 0.1 | 18.18 |  |
| *Colletotrichum musae* (Berk & Curt) Arx | 20 | 85.82 | 1.6555 |
|  | 10 | 78.72 |  |
|  | 5 | 64.54 |  |
|  | 1 | 37.23 |  |
|  | 0.1 | 19.15 |  |
| *Botryodiplodia theobromae* | 20 | 83.97 | 3.6962 |
|  | 10 | 65.85 |  |
|  | 5 | 51.57 |  |
|  | 1 | 31.71 |  |
|  | 0.5 | 14.63 |  |
| *Cladosporium cucumerinum* Ellis et Arthur | 20 | 84.86 | 4.844 |
|  | 10 | 72.11 |  |
|  | 5 | 54.98 |  |
|  | 2.5 | 28.29 |  |
|  | 1 | 6.77 |  |
| *Periconia hevenae* | 15 | 81.72 | 0.3775 |
|  | 10 | 77.61 |  |
|  | 5 | 74.25 |  |
|  | 1 | 66.42 |  |
|  | 0.1 | 33.21 |  |
| *Colletotrichum gloeosporioides* | 20 | 87.24 | 6.9152 |
|  | 10 | 55.19 |  |
|  | 5 | 33.83 |  |
|  | 1 | 19.29 |  |
|  | 0.1 | 7.12 |  |
| *B. cinerea* | 10 | 88.09 | 1.0016 |
|  | 5 | 73.35 |  |
|  | 1 | 54.55 |  |
|  | 0.5 | 35.11 |  |
|  | 0.1 | 12.85 |  |
| *Diplodia natalensis* | 20 | 82.35 | 1.7048 |
|  | 10 | 73.68 |  |
|  | 5 | 60.68 |  |
|  | 1 | 40.25 |  |
|  | 0.1 | 20.74 |  |
| *Curvularia* | 15 | 80.60 | 0.5051 |
|  | 10 | 76.59 |  |
|  | 5 | 75.92 |  |
|  | 1 | 63.55 |  |
|  | 0.1 | 28.76 |  |

3. In Vivo Micro-Screening Assay

To further study the fungicidal spectrum of the compound of Formula (I), indoor in vivo micro-screening assay were carried out on cucumber gray mold, cucumber scab, cucumber sclerotinia rot, cucumber brown spot, pepper *phytophthora* blight, and rice sheath blight. The results showed that the compound of Formula (I) had good prevention and treatment effect on cucumber gray mold, cucumber scab, cucumber brown spot, and rice sheath blight.

1) Target Strains

Cucumber scab strain: HX; cucumber brown spot strain: SDHGHB060509; cucumber sclerotinia rot strain: HGJH; pepper *phytophthora* blight strain: NSGP; and rice sheath blight strain: WK-1.

Cucumber gray mold strain had three different resistant strains: F109 (anti-benzimidazole and its derivatives, sensitive to N-phenylcarbamate, dicarboximide, and pyrimidine amine); Q503001 (sensitive to benzimidazole and its derivatives, N-phenylcarbamate, dicarboximide, and pyrimidine amine); and SC504002 (sensitive to benzimidazole and its derivatives as well as dicarboximide, anti-N-phenylcarbamate and anti-pyrimidine amine).

2) Medication and Inoculation

Medicament to be tested and medicament of control groups were prepared as needed in a sunny morning. Cucumber gray mold, cucumber scab, cucumber brown spot, cucumber sclerotinia rot, and rice sheath blight were medicated by spray, and after air dry, pathogens of cucumber scab and of cucumber brown spot were inoculated through spraying spore suspension respectively, pathogens of cucumber gray mold, of cucumber sclerotinia rot, and of rice sheath blight were inoculated through lawn foliage. Pepper *phytophthora* blight was medicated and inoculated by root-irrigation. Subsequently, all seedlings were cultured in wet environment.

3) Investigation

After the disease of control groups were serious, spot area, disease index, and the diseased seedling rate were investigated to calculate the efficacy. Cucumber scab, cucumber brown spot, and pepper *phytophthora* blight were investigated by grading method. The spot extension area of cucumber gray mold and of rice sheath blight was investigated. The diseased seedling rate of cucumber sclerotinia rot was investigated.

Disease index=Σ(amount of infected diseased leaves in a grade×relative value of the grade)×100/ (total amount of leaves×9);

Diseased seedling rate (%)=(total amount of seedlings−amount of diseased seedlings)/total amount of seedlings×100%

Prevention and treatment effect (%)=(disease of control group−disease of experiment group)/disease of control group×100%

The results are listed in Table 5.

TABLE 5

Results of in vivo micro-screening test of Compound of Formula (I)

| Target | Medicament | Concentration (mg/L) | Spot area (mm²) or disease index | Efficacy (%) |
|---|---|---|---|---|
| Cucumber gray mold (F-109) | Compound of Formula (I) | 500 | 3.67 | 96.43 |
| | | 100 | 8.03 | 92.19 |
| | 25% Amistar SC | 125 | 8.65 | 89.82 |
| | CK | Clear water | 102.81 | — |
| Cucumber gray mold (SC504002) | Compound of Formula (I) | 500 | 5.64 | 90.67 |
| | | 100 | 6.82 | 88.71 |
| | 25% Amistar SC | 125 | 6.14 | 89.82 |
| | CK | Clear water | 60.46 | — |
| Cucumber gray mold (Q503001) | Compound of Formula (I) | 500 | 2.82 | 97.71 |
| | | 100 | 7.78 | 93.69 |
| | 25% Amistar SC | 125 | 8.53 | 93.09 |
| | CK | Clear water | 123.39 | — |
| Cucumber sclerotinia rot | Compound of Formula (I) | 500 | 34.65 | 58.88 |
| | | 100 | 70.08 | 16.84 |
| | 25% Amistar SC | 125 | 24.45 | 70.99 |
| | CK | Clear water | 84.27 | — |
| Cucumber scab | Compound of Formula (I) | 500 | 0 | 100.00 |
| | | 100 | 0 | 100.00 |
| | 25% Amistar SC | 125 | 4.44 | 91.31 |
| | CK | Clear water | 51.11 | — |
| Cucumber brown spot | Compound of Formula (I) | 500 | 4.44 | 89.10 |
| | | 100 | 6.11 | 85.00 |
| | 25% Amistar SC | 125 | 3.33 | 91.82 |
| | CK | Clear water | 40.74 | — |
| Pepper *phytophthora* blight | Compound of Formula (I) | 500 | 24 | 30.09 |
| | | 100 | 25.33 | 26.22 |
| | 25% Amistar SC | 125 | 10 | 70.87 |
| | CK | Clear water | 34.33 | — |
| Rice sheath blight | Compound of Formula (I) | 500 | 46.87 | 70.04 |
| | | 100 | 59.96 | 61.67 |
| | 25% Amistar SC | 125 | 86.43 | 44.74 |
| | CK | Clear water | 156.42 | — |

*F-109, SC504001, Q503001, cucumber sclerotinia rot, and pepper *phytophthora* blight referred to spot area (mm²), cucumber scab, cucumber brown spot, rice sheath blight referred to disease index.

Example 3

Acute Toxicity and Ames Test

Bioassay results showed that the compound of Formula (I) had good preventive effect on downy mildew and powdery mildew. The toxicological indexes of the compound were tested following the standard GB15670-1995 "Toxicological test methods of pesticides for registration" by Tongji Medical College, Huazhong University of Science and Technology. The results showed that the compound had low toxicity.

The results are listed in Table 6.

TABLE 6

Results of Acute Toxicity and Ames test of compound (I)

| No. | Items | Toxicity |
|---|---|---|
| 1 | Acute oral test | Male rat: $LD_{50} > 5000$ mg/kg<br>Female rat: $LD_{50} > 5000$ mg/kg<br>Low toxicity |
| 2 | Acute skin test | Male rat: $LD_{50} > 2000$ mg/kg<br>Female rat: $LD_{50} > 2000$ mg/kg<br>Low toxicity |
| 3 | Eye stimulation test | Mild stimulation on rabbit's eye |
| 4 | Skin stimulation test | No stimulation on rabbit's skin |
| 5 | Skin sensitization test | Weak allergen (grade I) on guinea pig skin |
| 6 | Ames test | Negative |
| 7 | Micronucleus Test of Mice Polychromatic Erythrocytes | Negative |
| 8 | Chromosome aberration test of mice spermatogonial | Negative |

Example 4

Environmental Assessment Test

After acute toxicity and Ames test had been finished, environmental toxicity test was conducted following "Guideline for Environmental Safety Evaluation of Chemical Pesticides" of Agriculture Ministry of China by Shenyang Chemical Research Institute/Supervision and Test Center for Pesticide Safety Evaluation and Quality Control. The results showed that the compound was environmentally friendly.

The results are listed in Table 7.

TABLE 7

Results of environmental toxicity test

| No. | Items | Toxicity |
|---|---|---|
| 1 | Acute toxicity test on zebra fish | $LC_{50}$ (24 hrs): 0.069 mg.a.i/L<br>$LC_{50}$ (48 hrs): 0.060 mg.a.i/L<br>$LC_{50}$ (72 hrs): 0.047 mg.a.i/L<br>$LC_{50}$ (96 hrs): 0.043 mg.a.i/L |
| 2 | Acute oral toxicity test on quail | $LC_{50}$ > 1100 mg/kg.bw |
| 3 | Acute contact toxicity test on bee | $LC_{50}$ (48 hrs) > 100 μg a.i./per bee |
| 4 | Toxicity test on silkworm after 96 hrs' administration | $LC_{50}$ (24 hrs) > 300.0 mg/kg mulberry leaves<br>$LC_{50}$ (48 hrs) > 300.0 mg/kg mulberry leaves<br>$LC_{50}$ (96 hrs) > 132.1 mg/kg mulberry leaves |

Example 5

Enzyme Activity Test

Take NADH oxidase (NOX), succinate-cytochrome C oxidase (SCO), and Complex III as target enzymes, the inhibitory activity of the compound of Formula (I) was tested. The results showed that, the compound had much higher inhibitory activity on NOX, SCO, and Complex III than azoxystrobin which functioned as a control agent, particularly on Complex III.

TABLE 8

Results of enzyme activity test of the compound of Formula (I)

| | $IC_{50}$ (nM) | | |
|---|---|---|---|
| Medicament | NOX[a] | SCO[a] | Complex III[b] |
| Compound of Formula (I) | 5.3 | 3.4 | 4 |
| Azoxystrobin | 27 | 13 | 200 |

[a] NOX is generally used to detect an inhibitor of Complex I and Complex III; SCO is generally used to detect an inhibitor of Complex II and Complex III. Thus, an inhibitor of Complex III should have inhibitory activity on the two enzymes.

[b] The test target is cytochrome bc1 complex of pig heart.

Example 6

Preparation of Emulsifier Concentrate

Materials:
1) (E)-methyl 3-methoxy-2-(2-((5-methoxy-benzothiazol-2-ylthio)methyl)phenyl)acrylate. (prepared following Example 1) having 98% active ingredient.
2) Emulsifier: pesticide emulsifier No. 500 and Tween 80 (both from market)
3) Cosolvent: DMF, DMSO, and acetone (all from market)
4) Stabilizer: epoxidized soybean oil (from market)
5) Solvent: toluene and xylene (both from market)

Emulsifier Concentrate 1

To a beaker (1000 mL), 50 g (100% basis) of the compound of Formula (I), 150 g of DMF, and 50 g of acetone were added and stirred for dissolution. To the solution, 25 g of pesticide emulsifier No. 500 and 50 g of Tween 80, 20 g of epoxidized soybean oil, and 655 g of toluene were added. Thus, the emulsifier concentrate 1 having 5 wt. % of the compound of Formula (I) was obtained and further packed.

Emulsifier Concentrate 2

To a beaker (1000 mL), 75 g (100% basis) of the compound of Formula (I), 150 g of DMF, and 50 g of acetone were added and stirred for dissolution. To the solution, 50 g of pesticide emulsifier No. 500 and 50 g of Tween 80, 20 g of epoxidized soybean oil, and 605 g of toluene were added. Thus, the emulsifier concentrate 2 having 7.5 wt. % of the compound of Formula (I) was obtained and further packed.

Emulsifier Concentrate 3

To a beaker (1000 mL), 100 g (100% basis) of the compound of Formula (I), 150 g of DMF, and 150 g of acetone were added and stirred for dissolution. To the solution, 50 g of pesticide emulsifier No. 500 and 50 g of Tween 80, 20 g of epoxidized soybean oil, and 480 g of toluene were added. Thus, the emulsifier concentrate 3 having 10 wt. % of the compound of Formula (I) was obtained and further packed.

Example 7

Field Efficacy Trial

On the basis of indoor activity evaluation, field efficacy trials of the compound of Formula (I) on cucumber downy mildew, cucumber powdery mildew, and melon powdery mildew were conducted. The results are listed in Tables 9-11.

TABLE 9

Efficacy of emulsifier concentrate 1 (comprising 5 wt. % of the compound of Formula (I)) on cucumber powdery mildew
(After three times' administration)

| Medicament | Active ingredient (mg/L) | No. | Disease index (%) prior to administration | At 7th day Disease index (%) | Efficacy (%) |
|---|---|---|---|---|---|
| Compound of Formula | 100 | 1 | 9.2 | 1.7 | 91.17 |
| | | 2 | 7.6 | 1.2 | 92.74 |

TABLE 9-continued

Efficacy of emulsifier concentrate 1 (comprising 5 wt. % of the compound of Formula (I)) on cucumber powdery mildew (After three times' administration)

| Medicament | | | | | |
|---|---|---|---|---|---|
| (I) | | 3 | 8.4 | 1.9 | 90.16 |
| | | 4 | 7.6 | 1.2 | 92.41 |
| | | Average | 8.2 | 1.5 | 91.67 |
| | 50 | 1 | 7.2 | 2.1 | 85.88 |
| | | 2 | 7.2 | 2.4 | 84.49 |
| | | 3 | 8.0 | 2.8 | 86.18 |
| | | 4 | 7.2 | 2.2 | 85.31 |
| | | Average | 7.6 | 2.4 | 85.63 |
| | 25 | 1 | 8.1 | 3.6 | 78.48 |
| | | 2 | 8.4 | 4.2 | 76.74 |
| | | 3 | 8.1 | 4.6 | 77.57 |
| | | 4 | 7.0 | 3.3 | 77.35 |
| | | Average | 7.9 | 3.9 | 77.54 |
| | 12.5 | 1 | 9.2 | 5.5 | 71.05 |
| | | 2 | 8.7 | 5.5 | 70.59 |
| | | 3 | 9.3 | 6.7 | 71.54 |
| | | 4 | 9.2 | 5.8 | 69.71 |
| | | Average | 9.1 | 5.9 | 70.50 |
| 25% Amistar SC | 167 | 1 | 7.4 | 2.7 | 82.33 |
| | | 2 | 8.2 | 2.8 | 84.11 |
| | | 3 | 7.7 | 3.2 | 83.58 |
| | | 4 | 7.1 | 2.3 | 84.44 |
| | | Average | 7.6 | 2.8 | 83.24 |
| CK | | 1 | 9.2 | 19.0 | |
| | | 2 | 8.7 | 18.7 | |
| | | 3 | 7.9 | 20.0 | |
| | | 4 | 8.6 | 17.9 | |
| | | Average | 8.6 | 18.9 | |

TABLE 9-continued

Efficacy of emulsifier concentrate 1 (comprising 5 wt. % of the compound of Formula (I)) on cucumber powdery mildew (After three times' administration)

| | | | At $14^{th}$ day | | At $21^{st}$ day | |
|---|---|---|---|---|---|---|
| Medicament | Active ingredient (mg/L) | No. | Disease index (%) | Efficacy (%) | Disease index (%) | Efficacy (%) |
| Compound of Formula (I) | 100 | 1 | 0.9 | 96.46 | 3.3 | 91.58 |
| | | 2 | 1.3 | 94.43 | 2.6 | 92.15 |
| | | 3 | 1.4 | 95.18 | 2.8 | 93.17 |
| | | 4 | 1.0 | 95.68 | 3.0 | 91.23 |
| | | Average | 1.2 | 95.23 | 2.9 | 91.52 |
| | 50 | 1 | 2.1 | 89.44 | 3.2 | 89.57 |
| | | 2 | 1.8 | 91.85 | 3.0 | 90.44 |
| | | 3 | 2.7 | 90.23 | 4.4 | 88.74 |
| | | 4 | 1.9 | 91.34 | 3.7 | 88.58 |
| | | Average | 2.1 | 90.99 | 3.6 | 89.45 |
| | 25 | 1 | 3.5 | 84.35 | 6.8 | 8030 |
| | | 2 | 4.2 | 83.71 | 6.8 | 81.42 |
| | | 3 | 4.8 | 82.85 | 8.0 | 79.79 |
| | | 4 | 3.5 | 83.59 | 6.2 | 80.32 |
| | | Average | 4.0 | 83.51 | 7.0 | 77.78 |
| | 12.5 | 1 | 6.4 | 74.80 | 12.6 | 67.88 |
| | | 2 | 6.3 | 76.40 | 12.0 | 68.34 |
| | | 3 | 7.8 | 75.73 | 13.9 | 69.40 |
| | | 4 | 6.6 | 76.45 | 12.3 | 70.29 |
| | | Average | 6.8 | 75.66 | 12.7 | 68.91 |
| 25% Amistar SC | 167 | 1 | 2.7 | 86.78 | 4.9 | 84.46 |
| | | 2 | 3.2 | 87.28 | 5.3 | 85.16 |
| | | 3 | 3.2 | 87.97 | 5.2 | 86.18 |
| | | 4 | 2.5 | 88.44 | 4.7 | 85.29 |
| | | Average | 2.9 | 87.57 | 5.0 | 85.34 |
| CK | | 1 | 25.4 | | 39.2 | |
| | | 2 | 26.7 | | 37.9 | |
| | | 3 | 27.3 | | 38.6 | |
| | | 4 | 26.2 | | 38.7 | |
| | | Average | 26.4 | | 38.6 | |

TABLE 10

Efficacy of emulsifier concentrate 1 (comprising 5 wt. % of the compound of Formula (I)) on cucumber downy mildew

| | | | At $12^{th}$ day after second administration | | |
|---|---|---|---|---|---|
| Medicament | Active ingredient (mg/L) | No. | Total leaves | Disease index | Efficacy (%) |
| Compound of Formula (I) | 100 | 1 | 34.0 | 0.98 | 83.71 |
| | | 2 | 32.0 | 1.39 | 76.93 |
| | | 3 | 32.0 | 0.69 | 88.46 |
| | | Average | 32.7 | 1.02 | 83.04 |
| | 50 | 1 | 32.0 | 1.04 | 82.70 |
| | | 2 | 32.0 | 1.74 | 71.16 |
| | | 3 | 32.0 | 1.39 | 76.93 |
| | | Average | 32.0 | 1.39 | 76.93 |
| | 25 | 1 | 32.0 | 1.74 | 71.16 |
| | | 2 | 32.0 | 2.08 | 65.39 |
| | | 3 | 32.0 | 1.74 | 71.16 |
| | | Average | 32.0 | 1.85 | 69.24 |
| 25% Amistar | 125 | 1 | 32.0 | 1.39 | 76.93 |
| | | 2 | 32.0 | 0.69 | 88.46 |
| | | 3 | 32.0 | 1.39 | 76.93 |
| | | Average | 32.0 | 1.16 | 80.77 |
| CK | | 1 | 32.0 | 1.16 | |
| | | 2 | 32.0 | 6.25 | |
| | | 3 | 32.0 | 5.90 | |
| | | Average | 32.0 | 6.02 | |

TABLE 10-continued

Efficacy of emulsifier concentrate 1 (comprising 5 wt. % of the compound of Formula (I)) on cucumber downy mildew

| Medicament | Active ingredient (mg/L) | No. | Total leaves | Disease index | Efficacy (%) | Total leaves | Disease index | Efficacy (%) |
|---|---|---|---|---|---|---|---|---|
| | | | At 5th day after third administration | | | At 9th day after third administration | | |
| Compound of Formula (I) | 100 | 1 | 32.0 | 2.08 | 81.99 | 48.0 | 8.10 | 78.08 |
| | | 2 | 32.0 | 2.43 | 78.99 | 48.0 | 7.18 | 80.58 |
| | | 3 | 32.0 | 3.13 | 72.99 | 48.0 | 6.02 | 83.72 |
| | | Average | 32.0 | 2.55 | 77.99 | 48.0 | 7.10 | 80.79 |
| | 50 | 1 | 32.0 | 3.47 | 69.99 | 48.0 | 10.65 | 71.19 |
| | | 2 | 32.0 | 4.51 | 60.99 | 48.0 | 7.18 | 80.58 |
| | | 3 | 32.0 | 3.82 | 66.99 | 48.0 | 8.33 | 77.45 |
| | | Average | 32.0 | 3.94 | 65.99 | 48.0 | 8.72 | 76.41 |
| | 25 | 1 | 32.0 | 4.86 | 57.99 | 48.0 | 12.04 | 67.43 |
| | | 2 | 32.0 | 4.51 | 60.99 | 48.0 | 10.42 | 71.82 |
| | | 3 | 32.0 | 4.86 | 57.99 | 48.0 | 12.04 | 67.43 |
| | | Average | 32.0 | 4.75 | 58.99 | 48.0 | 11.50 | 68.89 |
| 25% Amistar | 125 | 1 | 32.0 | 3.47 | 69.99 | 48.0 | 8.80 | 76.20 |
| | | 2 | 32.0 | 3.13 | 72.99 | 48.0 | 5.79 | 84.34 |
| | | 3 | 32.0 | 2.43 | 78.99 | 48.0 | 9.95 | 73.07 |
| | | Average | 32.0 | 3.01 | 73.99 | 48.0 | 8.18 | 77.87 |
| CK | | 1 | 32.0 | 12.85 | | 48.0 | 36.34 | |
| | | 2 | 32.0 | 10.42 | | 48.0 | 34.72 | |
| | | 3 | 32.0 | 11.46 | | 48.0 | 39.81 | |
| | | Average | 32.0 | 11.57 | | 48.0 | 36.96 | |

TABLE 11

Efficacy of emulsifier concentrate 1 (comprising 5 wt. % of the compound of Formula (I)) on melon powdery mildew

| Medicament | Active ingredient (mg/L) | Total leaves | Disease index | Total leaves | Disease index | Efficacy (%) |
|---|---|---|---|---|---|---|
| | | Prior to administration | | At 7th day after first administration | | |
| Compound of Formula (I) | 100 | 1394 | 6.29 | 1490 | 6.29 | 39.15 |
| | 50 | 1374 | 7.20 | 1452 | 7.92 | 35.77 |
| | 25 | 1412 | 6.97 | 1435 | 7.11 | 34.38 |
| | 12.5 | 1169 | 6.90 | 1416 | 8.80 | 27.16 |
| 25% Amistar SC | 125 | 1387 | 7.37 | 1499 | 7.54 | 37.81 |
| CK | | 1326 | 10.30 | 1306 | 17.42 | |

| Medicament | Active ingredient (mg/L) | Total leaves | Disease index | Efficacy (%) | Total leaves | Disease index | Efficacy (%) |
|---|---|---|---|---|---|---|---|
| | | At 7th day after second administration | | | At 14th day after second administration | | |
| Compound of Formula (I) | 100 | 1478 | 4.52 | 86.22 | 1339 | 19.45 | 63.47 |
| | 50 | 1483 | 10.88 | 75.54 | 1559 | 30.42 | 54.57 |
| | 25 | 1473 | 13.63 | 67.15 | 1523 | 31.50 | 47.00 |
| | 12.5 | 1545 | 13.44 | 61.65 | 1587 | 40.33 | 29.55 |
| 25% Amistar SC | 125 | 1497 | 10.31 | 74.87 | 1541 | 30.95 | 53.41 |
| CK | | 1283 | 48.66 | | 1505 | 75.36 | |

The invention claimed is:

1. A method for preventing and/or treating a plant disease, the method comprising applying a fungicidal composition to a plant in need thereof, wherein:

said fungicidal composition comprises a compound represented by Formula (I):

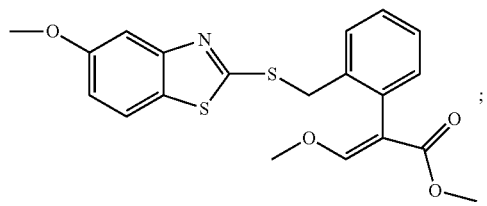

and said plant disease is powdery mildew, downy mildew, gray mold, brown spot, scab of vegetables and fruits, southern leaf blight of corn, rice false smut, citrus stem-end rot, or rape sclerotinia rot.

2. A method for preventing and/or treating a plant disease, the method comprising applying a fungicidal composition to a plant in need thereof, wherein:

said fungicidal composition comprises a compound represented by Formula (I),

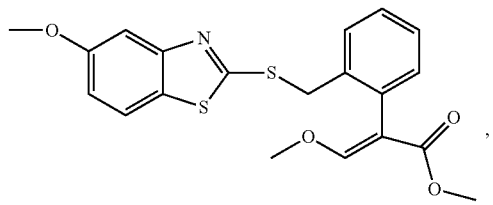

and further comprises an emulsifier, a cosolvent, a stabilizer, and a solvent;

wherein said emulsifier is polyoxyethylene sorbitan monooleate, polyoxyethylene sorbitan monostearate, ammonium styryl polyethenoxy ether sulfate, dibenzyl biphenyl polyoxyethylene ether, polyoxyethylene styrylphenyl ether having a polymerization degree of 15-30, styrenephenol polyethenoxy polyoxypropylene ether, nonylphenol polyethenoxy ether, alkylphenol formal polyethenoxy ether, diphenol polyethenoxy ether, or a mixture thereof; and said plant disease is powdery mildew, downy mildew, gray mold, brown spot, scab of vegetables and fruits, southern leaf blight of corn, rice false smut, citrus stem-end rot, or rape sclerotinia rot.

3. A method of treating and/or preventing downy mildew or gray mold in a plant, the method comprising applying an effective amount of a fungicidal composition to the plant, wherein said fungicidal composition comprises a compound represented by Formula (I):

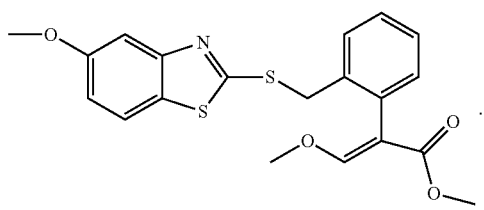

* * * * *